United States Patent [19]

Thomas et al.

[11] 4,242,572
[45] Dec. 30, 1980

[54] CONTACT LENS DISINFECTOR UNIT

[75] Inventors: Michael D. Thomas; Francis E. Ryder, both of Arab, Ala.

[73] Assignee: Ryder International Corporation, Arab, Ala.

[21] Appl. No.: 51,104

[22] Filed: Jun. 22, 1979

[51] Int. Cl.³ .......................... H05B 3/06; A61L 2/00
[52] U.S. Cl. ................................. 219/521; 422/199; 422/292; 422/300
[58] Field of Search ............... 422/292, 119, 199, 300; 219/438, 439, 441, 510, 512, 521; 221/276, 268; 242/198

[56] References Cited

U.S. PATENT DOCUMENTS

| | | | |
|---|---|---|---|
| 3,870,247 | 3/1975 | Carisey | 242/198 |
| 3,904,149 | 9/1975 | Suzuki | 242/198 |
| 3,916,442 | 10/1975 | Dattilo et al. | 242/198 |
| 4,044,226 | 8/1977 | Kadlecik et al. | 219/521 |
| 4,164,645 | 8/1979 | Dogliotti | 219/441 |

*Primary Examiner*—S. Leon Bashore
*Assistant Examiner*—Chris Konkol
*Attorney, Agent, or Firm*—Trexler, Wolters, Bushnell & Fosse

[57] ABSTRACT

A contact lens disinfector unit (10) includes a housing having a top wall (15), a heating block (27) within the housing for heating the contact lens case (25) and the lenses therein, and a lens case receiving compartment (26) between the heating block and the top wall (15) having an opening in a side wall (18) of the housing for slidingly receiving the contact lens case. A lens case ejector (28) is slidingly mounted on the housing top wall (15) and includes an elongate member (57) extending into the lens case receiving compartment to provide a key for positioning the lens case base against the heating block. The ejector also forms a pusher (56) to engage the lens case. A barrier wall (27a) isolates the lens case compartment from a cavity (48a) in the housing that contains electrical circuitry. Springs (50) press the lens case against the heating block.

7 Claims, 5 Drawing Figures

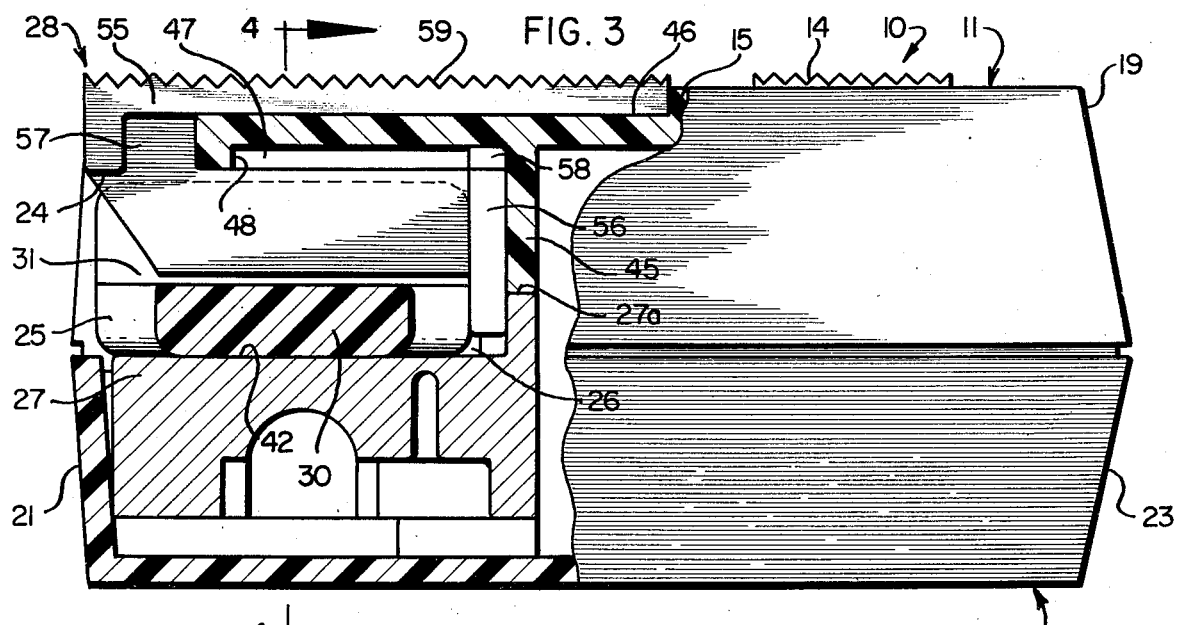
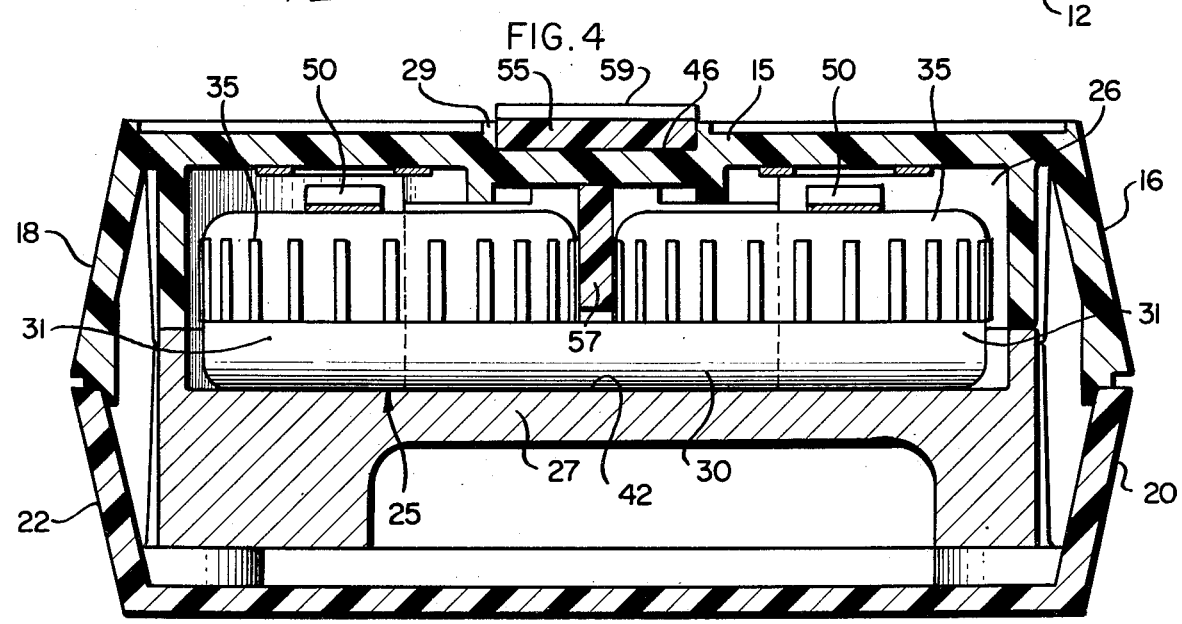
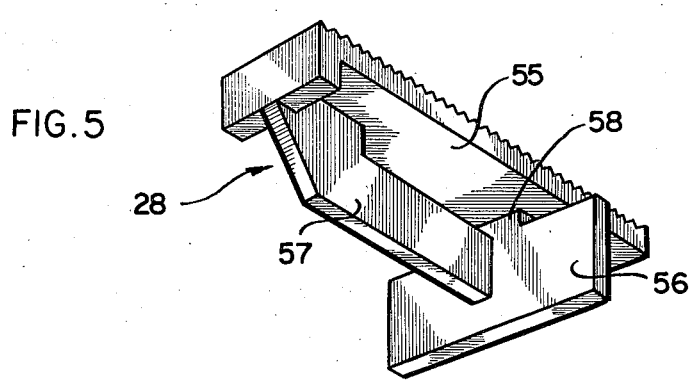

CONTACT LENS DISINFECTOR UNIT

BACKGROUND OF THE INVENTION

The present invention is directed to an improved contact lens disinfector unit.

Contact lenses, both of the hard and soft type, often must be disinfected before they are suitable for use. To this end, each contact lens of a pair is inserted into a separate container or receptacle for holding the right and left lenses spaced apart so that they do not become confused. A quantity of fluid is then administered to the containers and then the lens case comprised of the separate container is placed in a disinfector unit. The lens case is in direct contact with the heating block of the unit and the fluid within the containers is in direct contact with the lenses. After the disinfecting temperature has been reached and maintained for a sufficient period of time, the lens case and the contact lenses contained therein are permitted to cool before removal from the disinfector unit.

Prior contact lens disinfector units have relied upon gravitational forces for assuring that the contact lens cases are in contact with the disinfector unit heating block. While heat transfer from the heating blocks to the contact lens cases in these prior disinfector units has been adequate, increased heat transfer efficiency between the heating blocks and the contact lens cases would, of course, be desirable.

Furthermore, disinfector units of the prior art have generally included a hinged cover and a lens case recess having a bottom surface formed by the heating block. In order to place a lens case into such a disinfector unit, it is first necessary to lift the hinged cover to expose the recess, place the lens case in the recess so that the bottom of the case engages the surface of the heating block, and then close the hinged cover. For removing the lens case from the disinfector unit, it is necessary to lift the hinged cover, manually grab the lens case and then reclose the hinged cover. While disinfector units of this variety have proved to be generally successful, the hinged cover arrangement of these disinfector units have not maximized the convenience of using such units. Furthermore after the disinfection of the lenses has been completed, the lens case may still be hot to the touch. Obviously, should the user grab the contact lens case before it has cooled sufficiently, injury to the operator may result.

It is therefore a general object of the present invention to provide a new and improved contact lens disinfector unit which assures increased heat transfer efficiency between the heating block and the contact lens case.

It is a further object of the present invention to provide a new and improved contact lens disinfector unit wherein the contact lens case may be received within the disinfector unit against the heating block with greater ease.

It is a still further object of the present invention to provide a contact lens disinfector unit which includes an improved ejector mechanism for removing the contact lens case from the disinfector unit without requiring the operation to touch the lens case as it is ejected from the disinfector unit.

The device embodying the invention includes a housing, a heating block within the housing for heating a lens case and the contact lenses therein, a lens case receiving compartment within the housing adjacent to the heating block and having an opening permitting sliding insertion of the lens case into the compartment for surface contact with the heating block, and ejector means actuable externally of the housing and including pusher means for causing the lens case to slide out of the compartment through the opening.

The present invention further provides such a disinfector unit which includes biasing means within the contact lens case receiving compartment for urging the lens case against the heating block to increase heat transfer efficiency from the heating block to the contact lens case.

The invention further provides a barrier wall between the lens case compartment and the region of the housing that contains electrical circuitry that reduces the possibility of electric shock and aids in heating the lens case.

BRIEF DESCRIPTION OF THE DRAWINGS

FIG. 3 is a partial cross sectional view taken generally along lines 3—3 of FIG. 1;

FIG. 4 is a cross sectional view taken along lines 4—4 of FIG. 3; and

FIG. 5 is a perspective view of a lens case ejector that forms part of the present invention.

DESCRIPTION OF THE PREFERRED EMBODIMENT

Figure 1:
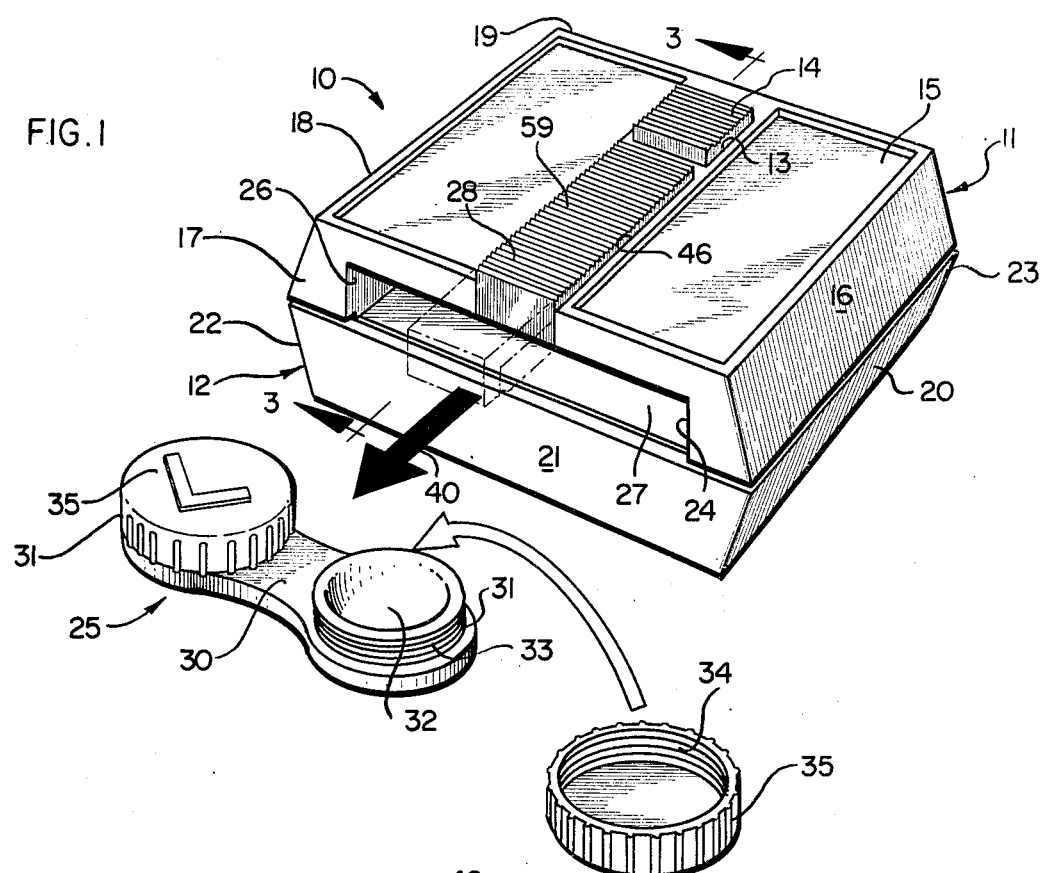
FIG. 1 is a perspective view of a contact lens disinfector unit embodying the present invention showing a contact lens case after being ejected therefrom and with a cap removed from one of the lens case receptacles.

Referring now to FIG. 1, a disinfector unit 10 includes a housing comprised of a top cover section 11, a bottom section 12, with an opening 13 provided in said cover section 11. In the opening 13 there is an activator button 14 mechanically coupled to a thermocouple switch (not shown). When the button 14 is depressed, a disinfecting cycle is initiated as a result of known circuitry. Beneath the button 14 there is a light bulb which lights up when the thermocouple switch is closed, thus indicating that the unit 10 is in the heating mode. The light bulb beneath the button 14 is shut off when the thermocouple switch opens at which time the unit 10 has reached the disinfecting temperature. The top cover section 11 further includes a top wall 15 and a plurality of side walls 16, 17, 18 and 19. The bottom section 12 correspondingly includes a plurality of side walls 20, 21, 22 and 23. The side walls of the top section 11 and the side walls of the bottom section 12 are arranged to interfit together as best seen in FIGS. 3 and 4 so as to form the housing of the disinfector unit 10.

Within the side wall 17 there is a rectangular opening 24 which is dimensioned to receive the contact lens case 25. The opening 24 provides access to a contact lens case receiving compartment 26. The compartment 26 is located between a heating block 27 and the top wall 15 of the unit 10. The heating block 27 is heated by an electric resistance (not shown) in a conventional manner.

Within the top wall 15 there is disposed a contact lens case ejector 28 of resilient plastic. The ejector 28 is mounted on the top wall for sliding movement from a position shown in full lines to a position shown in phantom lines (FIG. 1) for ejecting the lens case 25 from the disinfector unit compartment 26 in a manner to be described in greater detail hereinafter.

The lens case 25 is of the type which includes a base 30 and a pair of spaced apart cylindrical lens receiving receptacles 31, 31. The receptacles 31 each include a hollowed out portion 32 for receiving a respective one of the contact lenses and an external thread 33. The external thread 33 mates with an internal thread 34 carried by receptacle caps 35. The caps may be marked R and L to designate the receptacles for right and left eye lenses of the user.

In use, when it is desired to disinfect a pair of contact lenses, the user places each lens in a respective one of the receptacles 31 and then administers an amount of fluid to the receptacles. Thereafter, the caps 35 are mounted in place to enclose the contact lenses and the fluid. The lens case 25 is then slid into the compartment 26 through the opening 24 whereupon the base 30 makes direct surface contact with the heating block 27. The ejector 28, as will be more fully described hereinafter, is structured to permit the lens case 25 to be received by the compartment 26 only in the orientation shown in FIG. 1 so that it is assured that the base portion 30 will be in direct surface contact with the heating block 27. Once the lens case 25 has been inserted into the compartment 26, the button 14 is depressed to initiate a disinfecting cycle. Because the heating block 27 is in direct surface contact with the base 30. The lens case 25 and fluid therein will be heated to an elevated temperature. To assure sufficient heat transfer between the heating block 27 and the contact lens case 25 the disinfector unit 10 further includes leaf springs 50, 50 secured to the under surface of the top wall 15 and arranged to bias or urge the contact lens case 25 downwardly against the heating block 27 in a manner to be more fully described hereinafter.

After the disinfecting cycle has been completed and the lens case has been cooled, it is now time to remove the contact lens case 25 from the compartment 26. To that end the ejector 28 is displaced in the direction of the arrow 40 to the phantom line position shown in FIG. 1. The ejector 28 includes a pusher 56 within the compartment 26 which engages the contact lens case 25 for pushing the lens case and causing the case to slide out of the compartment 26 through the opening 24. An internal stop 48 for the ejector 28 causes the pusher to terminate its pushing force upon the lens case 25 at a point when the lens case 25 is approximately half way through the opening 24. At this point, the lens case rests on the edge of wall 21, which is lower edge of the opening 24. The lens case may then be manually removed from the disinfector unit housing.

Figure 2:
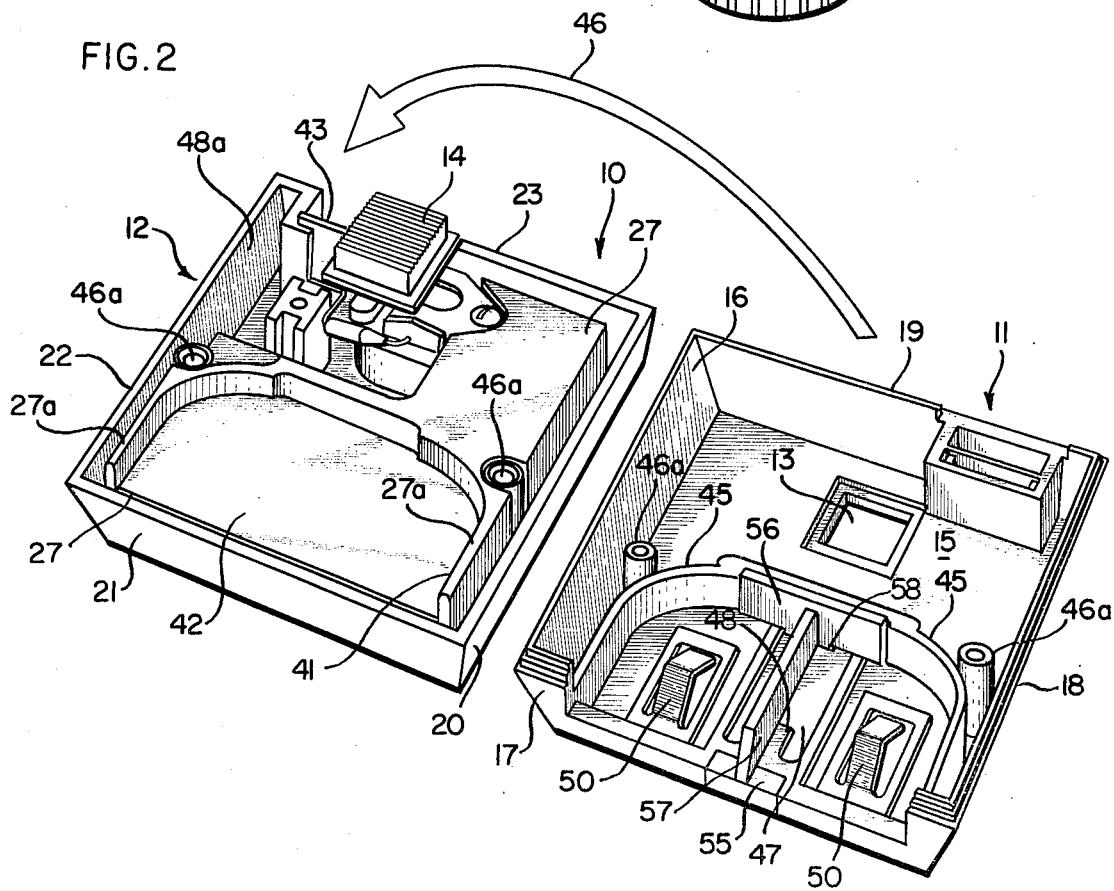
FIG. 2 is a perspective view showing the top and bottom halves of the unit separated to see the interior of the disinfector unit of FIG. 1.

Referring now to FIG. 2, the disinfector unit 10 is there shown with its top section 11 removed from the bottom section 12 so as to render visible the interior of the disinfector unit 10. Basically, the disinfector unit 10 includes the aforementioned heating block 27 which includes a recessed portion 41 for receiving, in part, the contact lens case 25. A conventional power supply circuit which includes a resistive heating element (not shown) is adapted to be connected to an electric power source by a known type of connector 43. The power supply circuit and resistive heating element combine to heat the heating block 27 to a temperature which is sufficient to cause the contact lenses to be disinfected. The heating block 27 includes a surface portion 42 which engages the under surface of the lens case base 30 during the heating of the contact lenses.

As shown in FIG. 2, the top section 11 includes an inner wall structure 45 which, when the top section 11 and bottom section 12 are brought together as illustrated by the arrow 46, coacts with the recess 41 to form the contact lens case receiving compartment 26. These sections 11, 12 are held together by screws (not shown) that pass through bosses 46a. Secured to the under surface of the top wall 15 are a pair of leaf springs 50. The leaf springs 50 project into the compartment 26 and are arranged to engage a respective one of the caps 35 of the lens case 25. As a result, the leaf springs 50 serve to bias or urge the base 30 of the case 25 against the heating block 27 despite variations in the heights of the cups 35. This arrangement insures efficient heat transfer from the heating block 27 to the case 25. In FIG. 4, the leaf springs 50 are shown in an operative position in which they are engaged with the caps 35 of the lens case 25 so as to urge the base portion 30 of the case against the heating block 27. The wall structure 45 coacts with the adjacent surface 27a of the heating block to form a barrier between the compartment 26 and the rear cavity 48a of the section 12 below the button 14, it being noted that the cavity 48a contains electrical wiring and circuit components. Thus, the cavity 48a is isolated to reduce electric shock possibilities. Also, the surface 27a is at a margin of the heater block 27 and extends substantially to the opening 24 whereby the barrier wall substantially surrounds the lens case except at the opening 24. Thus, the barrier helps to compensate for heat losses through the opening 24.

Referring now to FIGS. 1, 2 and 5, it can be seen that the ejector 28 includes a first member 55, a second member 56, and a third elongate member 57. The first member 55 and third member 57 form a bifurcated structure. The second member 56 is carried by the third member 57 and is disposed substantially perpendicular to the third member 57. The second member 56 includes an extension 58 which projects upwardly towards the first member 55.

As best seen in FIG. 3, the top wall 15 includes a first recess 46 which is arranged to receive the first member 55. The first member 55 has a knurled surface 59 which projects beyond the top wall 15. The first recess 46 is dimensioned in correspondence to the width dimension of the first member 55 to guide the sliding movement of the ejector. Additionally, a second recess 47 is provided in the under surface of the top wall 15 for receiving the extension 58 of the second member 56. By virtue of the bifurcated structure of the first and third members 55 and 57, the resiliency of the connection therebetween and because of the spacing between the first member 55 and second member extension 58, the ejector 28 is arranged to snap fit between the top wall 15 within the recesses 46 and 47 so as to mount the ejector for sliding movement on the top wall 15 of the unit 10.

Referring now to FIGS. 3 and 4, it can there be seen that the third member 57 is substantially perpendicular to the first member 55 and extends into the contact lens receiving compartment 26. More specifically, the third member 57 extends partially into the compartment 26 between the contact lens receptacles 31 of the lens case 25. As will be noted in FIG. 4, the third member 57 provides a key by which the lens case 25 can only be slid into the compartment 26 in the manner shown with its base portion 30 against the heating block 27. Thus, the third member 57 not only provides a key for guiding the movement of the lens case 25 into the compartment 26, but also limits the use of the disinfector unit 10 to those lens cases which are of the proper geometry and which, in turn, may be those lens cases that can withstand the elevated temperatures of the heating block 27.

The third member 57 also performs additional functions in that it defines a partition wall between the contact lens receptacles 31 and coacts with the base portion 30 of the lens case 25 to form substantially closed half sections of the compartment 26. The partition wall defined by the third member 57 therefore may to some degree limit the ingress of external air into the compartment 26 which would otherwise reduce the effectiveness of the heating of the contact lens case 25.

As will be noted in FIG. 3, the second member 56 is in engagement with the contact lens receptacles 31. As the ejector 28 is caused to be displaced from its solid line position as shown in FIG. 1 to its phantom line position, the second member 56 serves as a pusher to push the contact lens case 25 out of the compartment 26 through the opening 24. The recess 47 includes the stop surface 48 that engages the extension 58 when the ejector is at its fully displaced position as shown in phantom in FIG. 1. The surface 48 and extension 58 engage at a point where the lens case 24 is partially ejected through the opening 24 where it may rest in a position disposed for complete manual removal.

The invention is claimed as follows:

1. A unit for disinfecting contact lenses contained within a relatively flat lens case comprising: a housing having a lateral opening in one side thereof, a heating block disposed within said housing and including a horizontal support surface and a vertical wall surface, said heating block and said housing cooperating to define a lens case receiving compartment, with said lateral opening in said housing leading to said compartment and permitting the sliding insertion of a lens case into said compartment for disposition on said heater block support surface with said vertical wall surface providing a stop for said case as well as an end wall for said compartment, and ejector means slidably mounted to said housing and operable from the exterior of said housing for pushing a lens case outwardly of said compartment through said housing opening.

2. A disinfector unit as defined in claim 1 wherein said ejector means includes a first portion projecting beyond the periphery of said housing, and a second portion arranged internally of said compartment to engage the lens case within said compartment, and wherein said ejector means may be manipulated manually to eject a lens case from said housing.

3. A unit for disinfecting contact lenses as defined in claim 1, in combination with a lens case having a base and a pair of spaced apart lens receptacles projecting from said base, and said ejector means including an elongate portion extending into said compartment and disposed generally transverse to said heater block support surface but terminating short of said surface, such that said portion may be disposed between said lens receptacles with said base passing thereunder, said elongate portion providing means for positioning the lens case within the compartment, and forming a partition between the respective lens receptacles.

4. A unit for disinfecting contact lenses according to claim 1, wherein said vertical wall surface of said heater block serves as a barrier wall to isolate said lens case receiving compartment from that portion of said housing which accommodates electrical circuitry for effecting the heating cycle.

5. A disinfector unit as defined in claim 1 further including biasing means within said compartment for urging the lens case against said heating block.

6. A unit for disinfecting contact lenses contained within a lens case having a base and a pair of spaced apart lens receptacles on the base, said disinfector unit comprising: a housing having a top wall and at least one side wall; a heating block within said housing; a lens case receiving compartment between said heating block and said top wall and having an opening in said side wall; and pusher means slidingly mounted on said top wall and including an elongate member extending into said compartment and disposed between said lens receptacles to provide a key for positioning the lens case base relative to said heating block and forming a partition therebetween within said compartment, and a member forming part of said pusher means for engaging the lens case to eject the lens case from said housing through said opening.

7. A disinfector unit as defined in claim 6 further comprising a pair of leaf springs secured to said top wall within said compartment on opposite sides of said elongate member and arranged to act upon said receptacles respectively for urging the lens case base against said heating block.

* * * * *